US011191980B2

(12) United States Patent
Falkovskiy

(10) Patent No.: US 11,191,980 B2
(45) Date of Patent: Dec. 7, 2021

(54) AUTOMATED MAGNETIC RESONANCE IMAGE SEGMENTATION FOR ULTRASOUND THERMAL THERAPY CONTROL

(71) Applicant: Profound Medical Inc., Mississauga (CA)

(72) Inventor: Pavel Falkovskiy, Lausanne (CH)

(73) Assignee: Profound Medical Inc., Mississauga (CA)

(*) Notice: Subject to any disclaimer, the term of this patent is extended or adjusted under 35 U.S.C. 154(b) by 44 days.

(21) Appl. No.: 16/859,740

(22) Filed: Apr. 27, 2020

(65) Prior Publication Data

US 2021/0330993 A1 Oct. 28, 2021

(51) Int. Cl.
*G06K 9/00* (2006.01)
*A61N 7/02* (2006.01)
*G06T 7/00* (2017.01)
*G06T 7/11* (2017.01)

(52) U.S. Cl.
CPC .............. *A61N 7/02* (2013.01); *G06T 7/0012* (2013.01); *G06T 7/11* (2017.01); *G06T 2207/10088* (2013.01); *G06T 2207/20081* (2013.01); *G06T 2207/20084* (2013.01)

(58) Field of Classification Search
CPC ........... A61N 7/02; G06T 7/11; G06T 7/0012; G06T 2207/10088; G06T 2207/20084; G06T 2207/20081
USPC ....................................................... 382/156
See application file for complete search history.

(56) References Cited

U.S. PATENT DOCUMENTS

| 8,088,067 B2 | 1/2012 | Vortman et al. | |
|---|---|---|---|
| 10,194,829 B2 | 2/2019 | Kaditz et al. | |
| 2010/0036246 A1* | 2/2010 | Kushculey | A61N 7/02 600/439 |
| 2010/0168551 A1* | 7/2010 | Moller | A61B 5/1075 600/407 |
| 2011/0144545 A1* | 6/2011 | Fan | A61N 7/02 601/3 |
| 2011/0218464 A1* | 9/2011 | Iger | A61B 18/14 601/2 |

(Continued)

OTHER PUBLICATIONS

Mougenot et al., "Quantification of near-filed heating during volumetric MR-HIFU ablation", Med. Phys., 2011, p. 272-282, vol. 38, American Association of Physicists in Medicine.

(Continued)

*Primary Examiner* — Van D Huynh
(74) *Attorney, Agent, or Firm* — Intrinsic Law Corp.

(57) ABSTRACT

A system and method for acquiring magnetic resonance (MR) images, with an MR system, of tissue proximal to a target treatment region in a patient, the tissue including a non-spatially uniform subcutaneous fat layer; in a computer comprising a hardware-based processor, automatically determining a thickness of the subcutaneous fat layer using a trained neural network, the neural network trained using manually-segmented MR images from previous patients; in the computer, automatically adjusting a treatment parameter based on the thickness of the subcutaneous fat layer; and delivering thermal therapy to the target treatment region with a high-intensity focused ultrasound system based on the adjusted treatment parameter.

20 Claims, 11 Drawing Sheets

(56) References Cited

U.S. PATENT DOCUMENTS

| | | | | |
|---|---|---|---|---|
| 2012/0157842 A1* | 6/2012 | Davis | ............... | A61N 7/02 |
| | | | | 600/439 |
| 2012/0172708 A1* | 7/2012 | Anand | ............... | A61N 7/02 |
| | | | | 600/411 |
| 2016/0175619 A1* | 6/2016 | Lee | ............... | A61N 7/02 |
| | | | | 601/3 |
| 2016/0192899 A1* | 7/2016 | He | ............... | A61B 8/5223 |
| | | | | 600/449 |
| 2018/0055478 A1* | 3/2018 | Choi | ............... | A61N 7/02 |
| 2018/0154184 A1* | 6/2018 | Kong | ............... | A61N 7/02 |
| 2019/0143149 A1 | 5/2019 | Sverdlik et al. | | |

OTHER PUBLICATIONS

Ronneberger et al., "U-Net: Convolutional Networks for Biomedical Image Segmentation", International Conference on Medical Image Computing and Computer-Assisted Intervention, 2015, p. 234-241, MICCAI.

WIPO, "International Search Report", PCT/CA2021/050540, dated Jun. 25, 2021.

\* cited by examiner

AUTOMATED MAGNETIC RESONANCE IMAGE SEGMENTATION FOR ULTRASOUND THERMAL THERAPY CONTROL

TECHNICAL FIELD

This application relates generally to process controls and controllers for imaged-guided high-intensity focused ultrasound (HIFU) systems and similar applications.

BACKGROUND

Image-guided HIFU systems are used to deliver thermal therapy to a target treatment volume or region in a patient. For example, HIFU-delivered thermal therapy can be used to non-surgically ablate undesirable tissue, such as tumors, that is disposed in the patient's body. The composition and properties of the patient's body in the nearfield region between the HIFU ultrasound transducers and the target treatment region can impact the HIFU treatment. For example, treatment of the target treatment region is often limited by the heating of the skin and subcutaneous fat tissue in the nearfield region, which can lead to undesired tissue damage. In existing systems, the temperature rise in near-field-region tissues is modeled by simulating the ultrasound beam and determining the spatial distribution of the temperature increase with the bioheat transfer equation.

The decision about the safety of a treatment can be made based on the expected temperature rise in the tissues. These approaches often model an average patient as a homogeneous media with some average tissue properties or as a stack of rectangular tissue slabs of predefined thicknesses. For example, the subcutaneous fat layer is modeled as a rectangular slab of tissue having a predefined thickness.

In principle, MR imaging can be used to measure the thickness of the subcutaneous fat layer. However, since the subcutaneous fat layer thickness is not uniform in the patient, there is limited value in using a measured subcutaneous fat layer thickness as a treatment parameter because it would apply to—and only be accurate for—one location only. It is not practical to have a user manually enter the subcutaneous fat layer thickness at multiple locations because it would take excessive time for the user to measure it or segment the subcutaneous fat layer.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a method for controlling delivery of thermal therapy, comprising: acquiring magnetic resonance (MR) images, with an MR imaging system, of tissue proximal to a target treatment region in a patient, the tissue including a non-spatially uniform subcutaneous fat layer; in a computer comprising a hardware-based processor, automatically determining an actual thickness of the subcutaneous fat layer using a trained neural network, the neural network trained using manually-segmented MR images from previous patients; in the computer, automatically adjusting a set of treatment parameters based on the actual thickness of the subcutaneous fat layer; and delivering thermal therapy to the target treatment region with a high-intensity focused ultrasound (HIFU) system based on the adjusted treatment parameters.

In one or more embodiments, the set of treatment parameters comprises an input to a safety control algorithm. In one or more embodiments, the safety control algorithm ensures a predetermined maximum temperature and/or a predetermined maximum thermal dose of tissue between the target treatment region and a therapeutic applicator of the HIFU system. In one or more embodiments, the safety control algorithm increases a cooldown time between thermal therapy sonications when the actual thickness of the subcutaneous fat layer is higher than a predetermined thickness, the predetermined thickness corresponding to an average subcutaneous fat layer thickness for the gender of the patient. In one or more embodiments, the safety control algorithm decreases a cooldown time between thermal therapy sonications when the actual thickness of the subcutaneous fat layer is lower than the predetermined thickness.

In one or more embodiments, the set of treatment parameters comprises a frequency of ultrasound energy generated by the HIFU system. In one or more embodiments, the set of treatment parameters comprises a power of ultrasound energy generated by the HIFU system. In one or more embodiments, the power of the ultrasound energy increases when the actual thickness of the subcutaneous fat layer is higher than a predetermined thickness, the predetermined thickness corresponding to an average subcutaneous fat layer thickness for the gender of the patient. In one or more embodiments, the power of the ultrasound energy decreases when the actual thickness of the subcutaneous fat layer is lower than the predetermined thickness. In one or more embodiments, the set of treatment parameters comprises a relative phase of ultrasound energy generated by each ultrasound transducer element in an array of ultrasound transducer elements.

Another aspect of the invention is directed to a system for delivering ultrasound thermal therapy comprising: a magnetic resonance (MR) imaging system; a high-intensity focused ultrasound (HIFU) system comprising an array of ultrasound transducer elements; a computer comprising a hardware-based processor, the computer operatively coupled to the MR imaging system and to the HIFU system; and a non-transitory storage medium comprising computer-readable instructions that, when executed by the processor, cause the processor to: send a first output signal to the MR system to acquire MR images of tissue proximal to a target treatment region in a patient, the tissue including a non-spatially uniform subcutaneous fat layer, automatically determine an actual thickness of the subcutaneous fat layer using a trained neural network, the neural network trained using manually-segmented MR images from previous patients, adjust a set of treatment parameters based on the actual thickness of the subcutaneous fat layer, and send a second output signal to the HIFU system to deliver thermal therapy to the target treatment region based on the adjusted treatment parameter.

In one or more embodiments, the set of treatment parameters comprises an input to a safety control algorithm. In one or more embodiments, the safety control algorithm ensures a predetermined maximum temperature and/or a predetermined maximum thermal dose of tissue between the target treatment region and a therapeutic applicator of the HIFU system. In one or more embodiments, the safety control algorithm increases a cooldown time between thermal therapy sonications when the actual thickness of the subcutaneous fat layer is higher than a predetermined thickness, the predetermined thickness corresponding to an average subcutaneous fat layer thickness for the gender of the patient. In one or more embodiments, the safety control algorithm decreases a cooldown time between thermal therapy sonications when the actual thickness of the subcutaneous fat layer is lower than the predetermined thickness.

In one or more embodiments, the set of treatment parameters comprises a frequency of ultrasound energy generated by the HIFU system. In one or more embodiments, the set of treatment parameters comprises a power of ultrasound energy generated by the HIFU system. In one or more embodiments, the power of the ultrasound energy increases when the thickness of the subcutaneous fat layer is higher than a predetermined thickness, the predetermined thickness corresponding to an average subcutaneous fat layer thickness for the gender of the patient. In one or more embodiments, the power of the ultrasound energy decreases when the thickness of the subcutaneous fat layer is lower than the predetermined thickness. In one or more embodiments, the set of treatment parameters comprises a relative phase of ultrasound energy generated by each ultrasound transducer element in the array of ultrasound transducer elements.

BRIEF DESCRIPTION OF THE DRAWINGS

For a fuller understanding of the nature and advantages of the present concepts, reference is made to the following detailed description of preferred embodiments in connection with the accompanying drawings.

DETAILED DESCRIPTION

The inventors have recognized that it would be desirable to automatically segment the subcutaneous fat layer at all locations in MR images and to produce a map of subcutaneous fat layer thickness (and other tissues by extension) which can then be used as a treatment parameter.

An artificial neural network or other machine learning is used to automatically segment MR images of the target treatment region and nearfield region. The MR images are automatically segmented as containing fat or as not containing fat. The artificial neural network is trained using manually-segmented images and optional synthetic images that are based on the manually-segmented images. The segmented MR images are used to determine the thickness of a non-spatially uniform subcutaneous fat layer in the nearfield. The subcutaneous fat thickness is used to adjust one or more treatment parameters.

Figure 1:
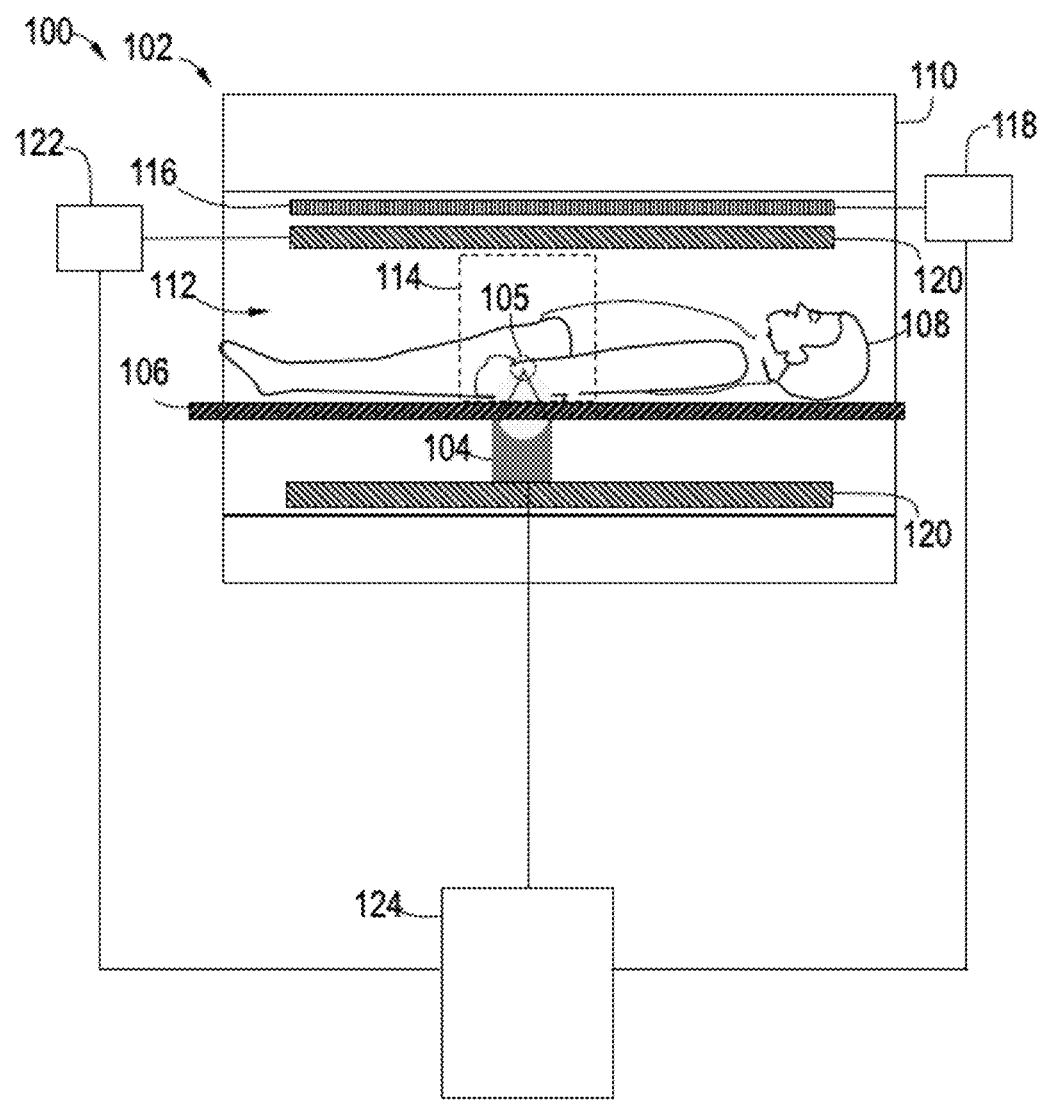
FIG. 1 is a diagram of one type of system in which at least some of the apparatus and/or methods disclosed herein are employed, in accordance with at least some embodiments.

FIG. 1 is a diagram of one type of a medical system 100 in which at least some of the apparatus, systems, and/or methods disclosed herein are employed, in accordance with at least some embodiments. The system 100 includes a patient support 106 for a patient 108, a magnetic resonance imaging system 102, and an image-guided HIFU system 104.

The magnetic resonance imaging system 102 includes a magnet 110 disposed about an opening 112, an imaging zone 114 in which the magnetic field is strong and uniform enough to perform magnetic resonance imaging, a set of magnetic field gradient coils 116 to change the magnetic field rapidly to enable the spatial coding of MRI signals, a magnetic field gradient coil power supply 118 that supplies current to the magnetic field gradient coils 116 and is controlled as a function of time, a transmit/receive coil 120 (also known as a "body" coil) to manipulate the orientations of magnetic spins within the imaging zone 114, a radio frequency transceiver 122 connected to the transmit/receive coil 120, and a computer 124. The computer 124 includes a hardware-based processor that executes computer-readable instructions (e.g., stored on a non-transitory storage medium operatively coupled to the computer 124) to perform tasks to facilitate operation of the MRI system 102. In addition, the computer 124 is coupled to the radio frequency transceiver 122, the magnetic field gradient coil power supply 118, and the image-guided energy delivery system 104.

The HIFU system 104 includes a therapeutic applicator comprising an array of ultrasonic transducer elements to perform image-guided thermal therapy (e.g., ultrasound therapy) in multiple angular directions to treat a target treatment region. The array of ultrasonic transducer elements are configured and arranged to have a geometric focus 105 that can be electronically steered by adjusting the relative phase of the ultrasound energy generated by each ultrasonic transducer element. The HIFU system 104 is imaged-guided to treat a target treatment region 105 in the patient 108.

The MRI computer 124 can include more than one computer in some embodiments, which can be dedicated for the MRI system 102. In at least some embodiments, the MRI computer 124 and/or one or more other computing devices (not shown) in and/or coupled to the system 100 may also perform one or more tasks (e.g., by executing computer-readable instructions stored on a non-transitory storage medium) to implement one or more aspects and/or embodiments disclosed herein (or portion(s) thereof) to determine the thickness of subcutaneous fat between the therapeutic applicator and the target treatment region and to adjust one or more treatment parameters based on the subcutaneous fat thickness.

One or more of the computers, including computer 124, can include a treatment plan for the patient 108 that includes the target treatment region and the desired or minimal energy (e.g., thermal) dose for the target treatment region. The computer(s) can use images from the magnetic resonance imaging system 102 to image guide the therapeutic applicator (e.g., position and angular orientation). The computer(s) can also use images from the magnetic resonance imaging system 102 to determine the subcutaneous fat thickness of the patient 108 proximal to the target treatment region (e.g., in the nearfield), for example using machine learning such as an artificial neural network. The subcutaneous fat thickness can be used to adjust the intensity/power of the ultrasound energy, the frequency of the ultrasound energy (e.g., the ultrasound frequency), the phase of the ultrasound energy, the duration of the sonication, and/or the minimum time to wait between sonications. Some or all of the foregoing computers can be in communication with one another (e.g., over a local area network, a wide area network, a cellular network, a WiFi network, or other network), for example through a software-controlled link to a communication network.

Figure 2:
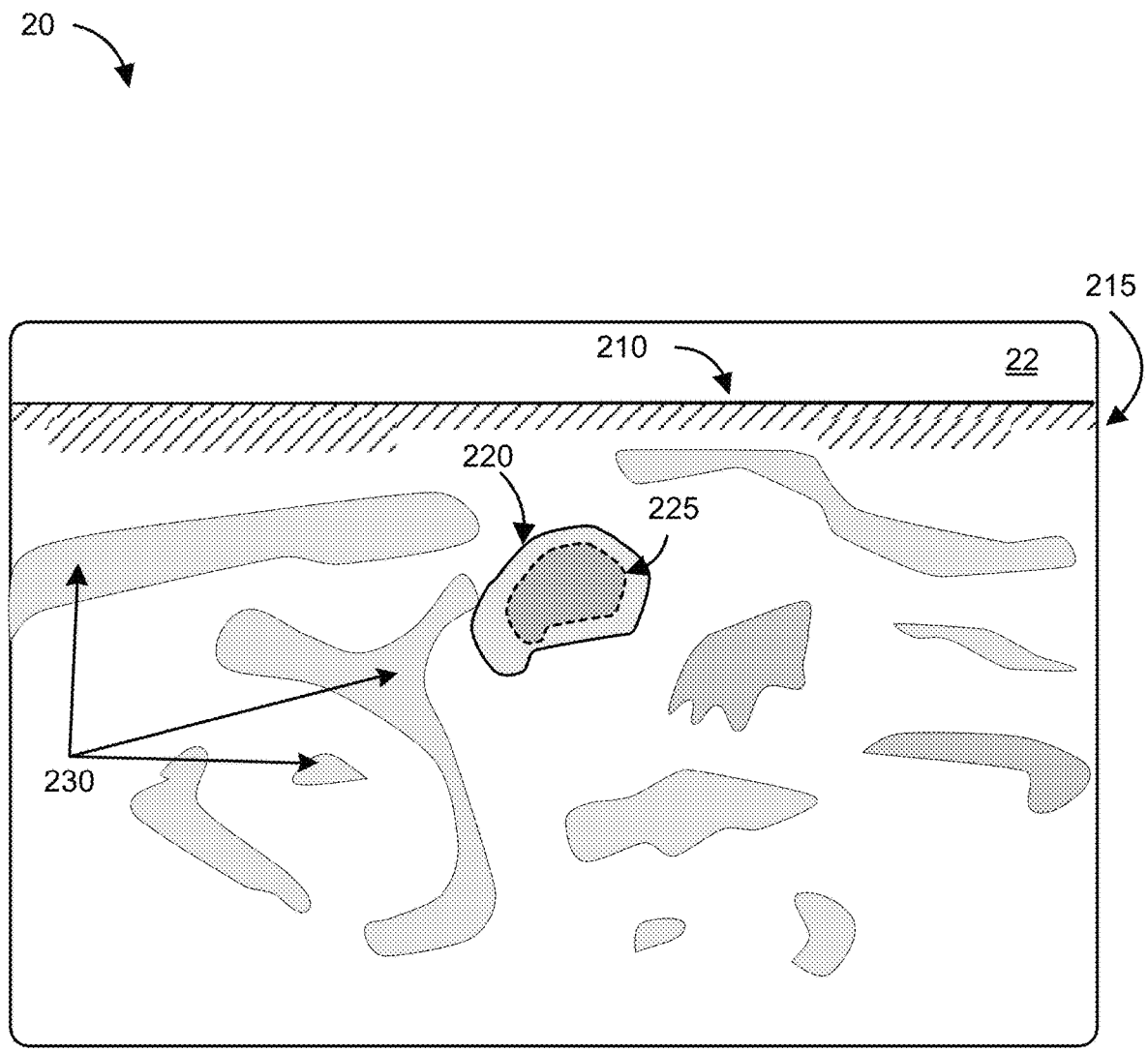
FIG. 2 illustrates an example of a T2-weighted cross-sectional MR image according to an embodiment.

FIG. 2 illustrates a T2-weighted cross-sectional image 22, taken using MRI system 102, of a portion of a patient's body in the vicinity of a treatment target volume. The scene shown includes, for example, a visual output device such as a computer monitor screen 20 or application window of a computer application program for displaying an image 22. The image 22 includes the patient's skin 210, subcutaneous fat 215, and target volume 220. The target volume 220 can comprise some or all of an organ (e.g., uterus, bladder, pancreas, or another abdominal organ), fibroids, a malignant tumor, or other volume. Various zones 230 in the patient's body are shown by a visual representation of their temperatures within image 22. The temperatures can be determined by MR thermometry or other technique. The zones 230 can be displayed on the screen 20 as colored contours, contour plots, gray scale intensities or other visual representations of the temperature and/or temperature uncertainty.

A treatment target boundary 225 is further shown on the image 22, which can be a contour of another color, a dashed contour, or other representation. The treatment target boundary 225 is the intended boundary within which the energy of the thermal treatment process is substantially controlled to a set-point temperature (or thermal dose) ensuring rapid and sufficient cell death of diseased cells within the interior of the volume defined by the treatment target boundary 225. Heat can be conducted outside the treatment target boundary 225 such as to subcutaneous fat 215 and skin 210. During HIFU treatment, multiple target locations within the target boundary 225 are sonicated in succession. At each target location, the ultrasound beam (or other means of delivering energy) traverses the skin 210, subcutaneous fat 215, and other tissues, and the thickness and location of each such tissue layer may differ based on the target location.

A safety control algorithm can be used to ensure that the subcutaneous fat 215, which is not spatially uniform in thickness, and skin 210 in the nearfield do not exceed a predetermined maximum temperature and/or a predetermined maximum thermal dose during the ultrasound therapy. The safety control algorithm calculates the expected temperature change during sonications and in the period between sonications, taking into account sonication parameters (e.g. ultrasound frequency, sonication power/intensity, and/or sonication duration) as well as the subcutaneous fat thickness proximal to the target sonication location. To ensure safety of the ultrasound therapy, the safety control algorithm may impose limits to the sonication parameters; the safety control algorithm may also enforce a minimum period between consecutive sonications. By taking into account the patient-specific variations in subcutaneous fat thickness, the ultrasound therapy may be optimal in terms of safety and/or efficiency.

In all, FIG. 2 shows a temperature map. Three-dimensional representations of the same can be constructed from additional layers, slices or cross-sectional views like that shown in FIG. 2. The methods described herein can therefore be generalized to three-dimensional space by stacking slices such as shown in FIG. 2 side by side to form a 3D volume without loss of generality.

Figure 3:
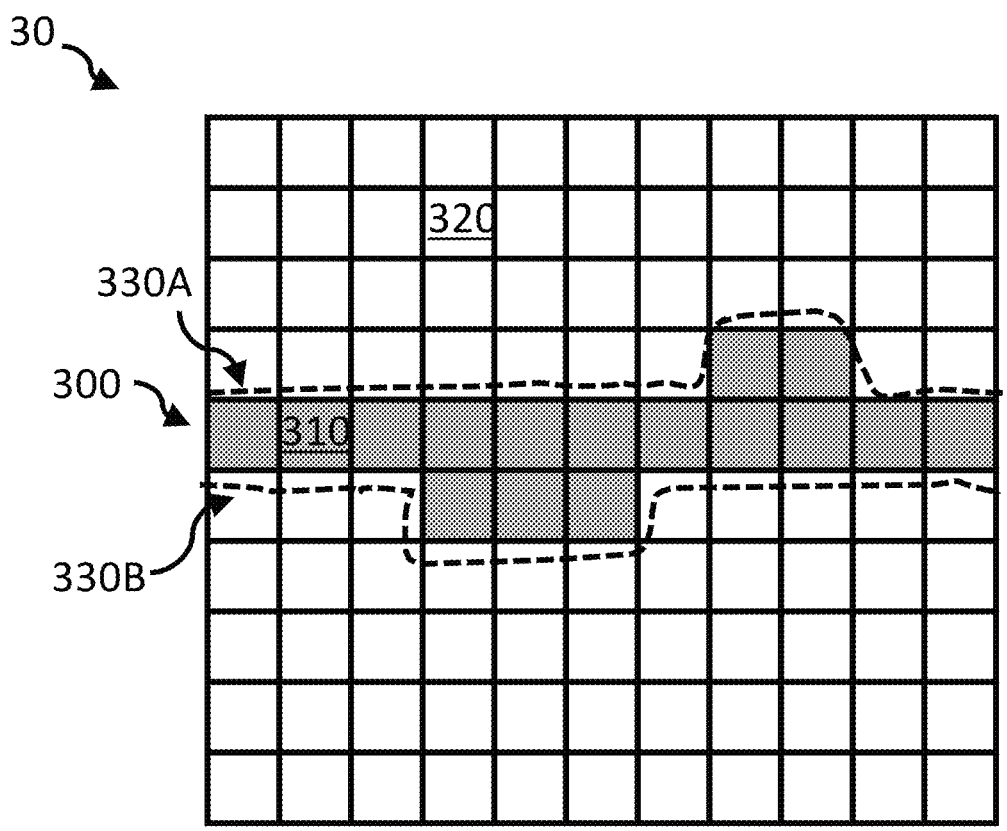
FIG. 3 illustrates a manually-classified T2-weighted image cross-sectional image according to an embodiment.

FIG. 3 illustrates a manually-segmented T2-weighted cross-sectional image 30 according to an embodiment. The image 30 includes a cluster or region 300 of voxels 310 corresponding to the patient's subcutaneous fat layer. The image 30 also includes voxels 320 that correspond to other portions of the patient's anatomy, such as the skin, an organ, and/or a tumor. The image is manually segmented for fat (e.g., subcutaneous fat) by drawing lines 330A, B between subcutaneous fat voxels 310 and the other voxels 320. The cross-sectional thickness of the subcutaneous fat layer is determined based on the distance between the segmentation lines 330A, B and/or on the dimensions of the classified voxels 310.

Figure 4:
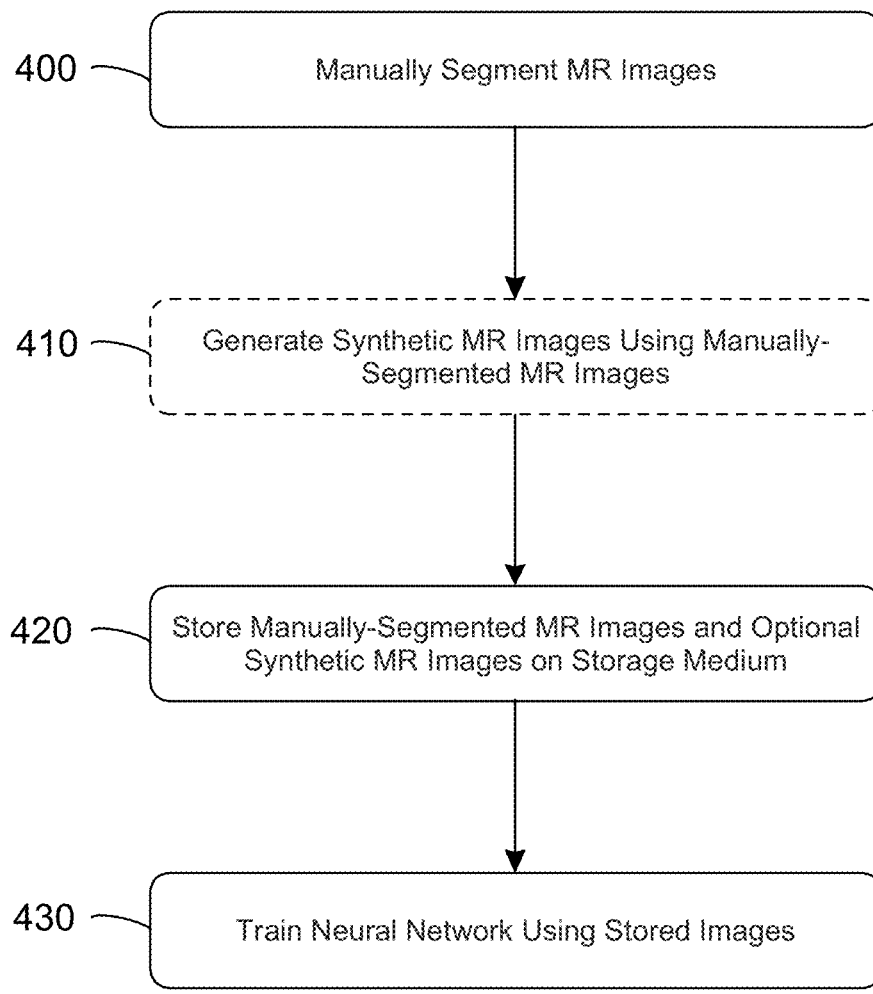
FIG. 4 is a flow chart of a method for training a neural network to automatically segment MR images that include fat according to one or more embodiments.

FIG. 4 is a flow chart 40 of a method for training a neural network to automatically segment MR images that include subcutaneous fat according to one or more embodiments. In step 400, existing MR images that include subcutaneous fat are manually segmented, for example as discussed above with respect to FIG. 3. For example, the existing MR images are segmented as having fat voxels (e.g., subcutaneous fat voxels) and non-fat voxels.

Figure 5:
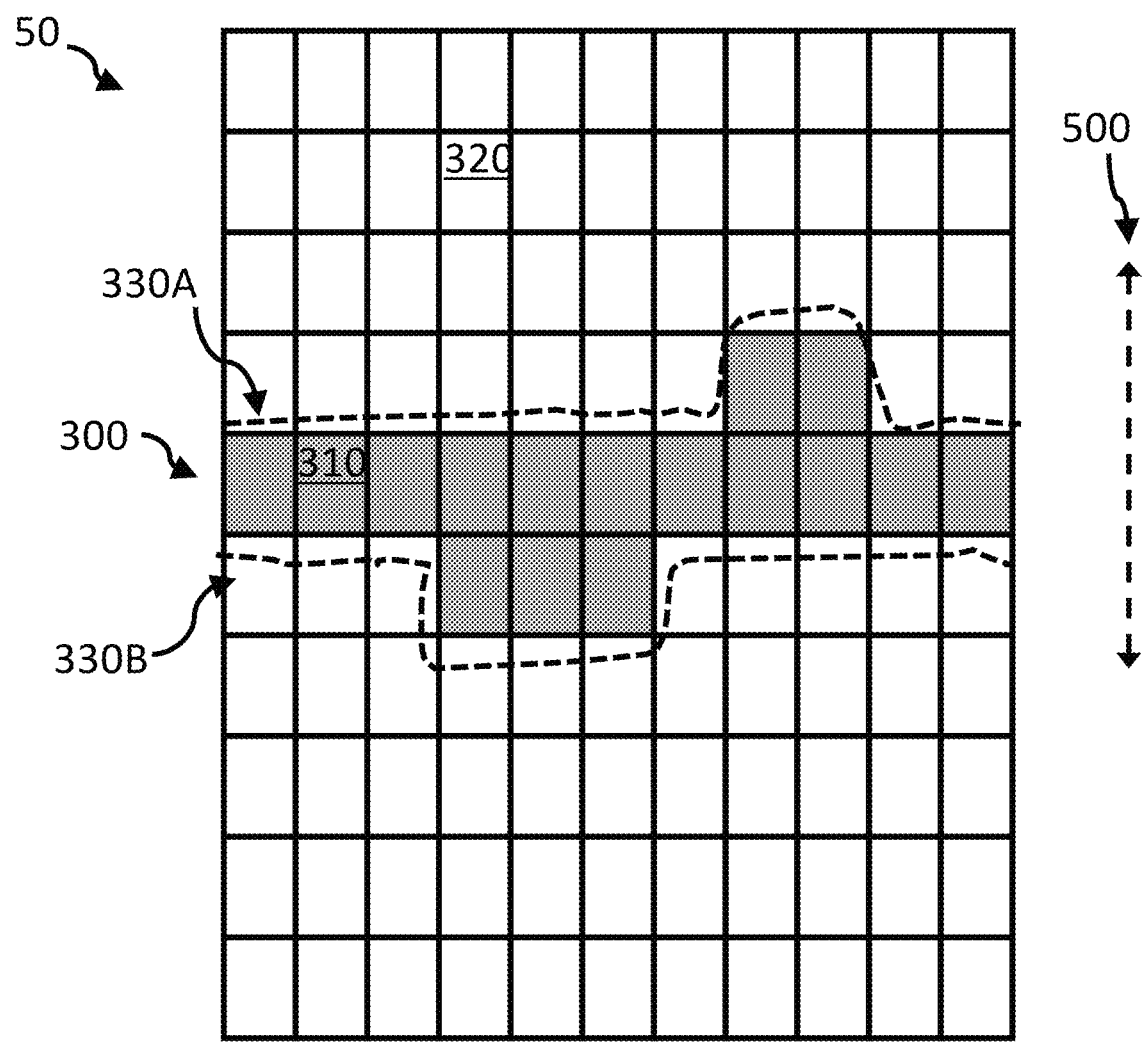
FIG. 5 illustrates a classified synthetic cross-sectional image that was generated by asymmetrically stretching the manually-classified image of FIG. 3 along a first axis.
Figure 6:
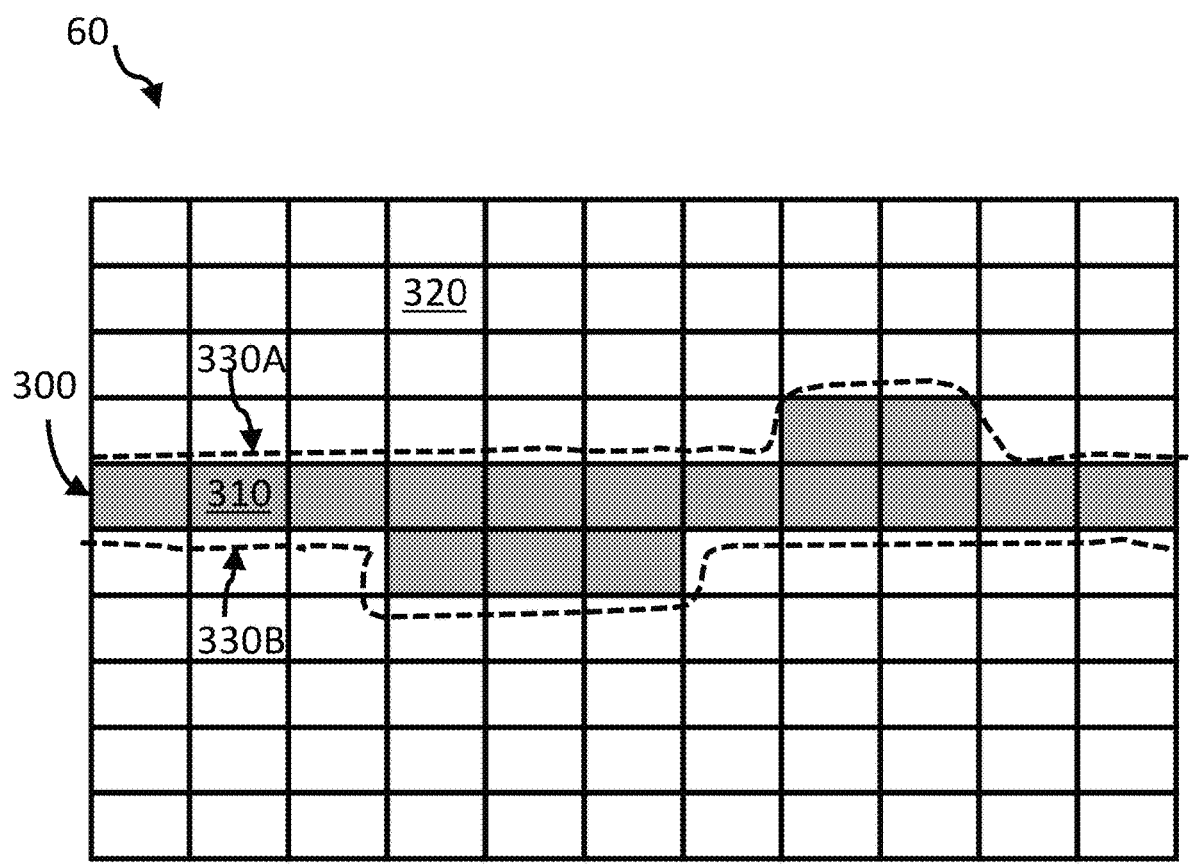
FIG. 6 illustrates a classified synthetic cross-sectional image that was generated by asymmetrically stretching the manually-classified image of FIG. 3 along a second axis that is orthogonal to the first axis.
Figure 6:
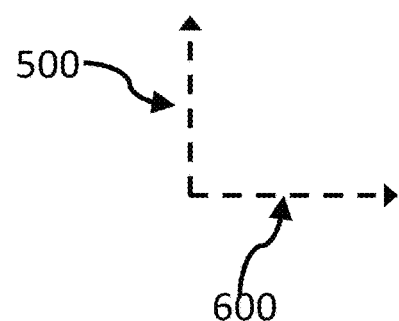

In optional step 410, synthetic MR images are generated based on some or all of the manually-segmented MR images. The synthetic MR images can be generated by stretching and/or rotating the manually-segmented MR images. For example, stretched images can be generated by asymmetrically stretching three-dimensional manually-segmented MR images along one, two, or three axes. FIG. 5 illustrates a classified synthetic cross-sectional image 50 that was generated by asymmetrically stretching image 30 along a first axis 500. FIG. 6 illustrates a classified synthetic cross-sectional image 60 that was generated by asymmetrically stretching image 30 along a second axis 600 that is orthogonal to the first axis 500.

Figure 7:
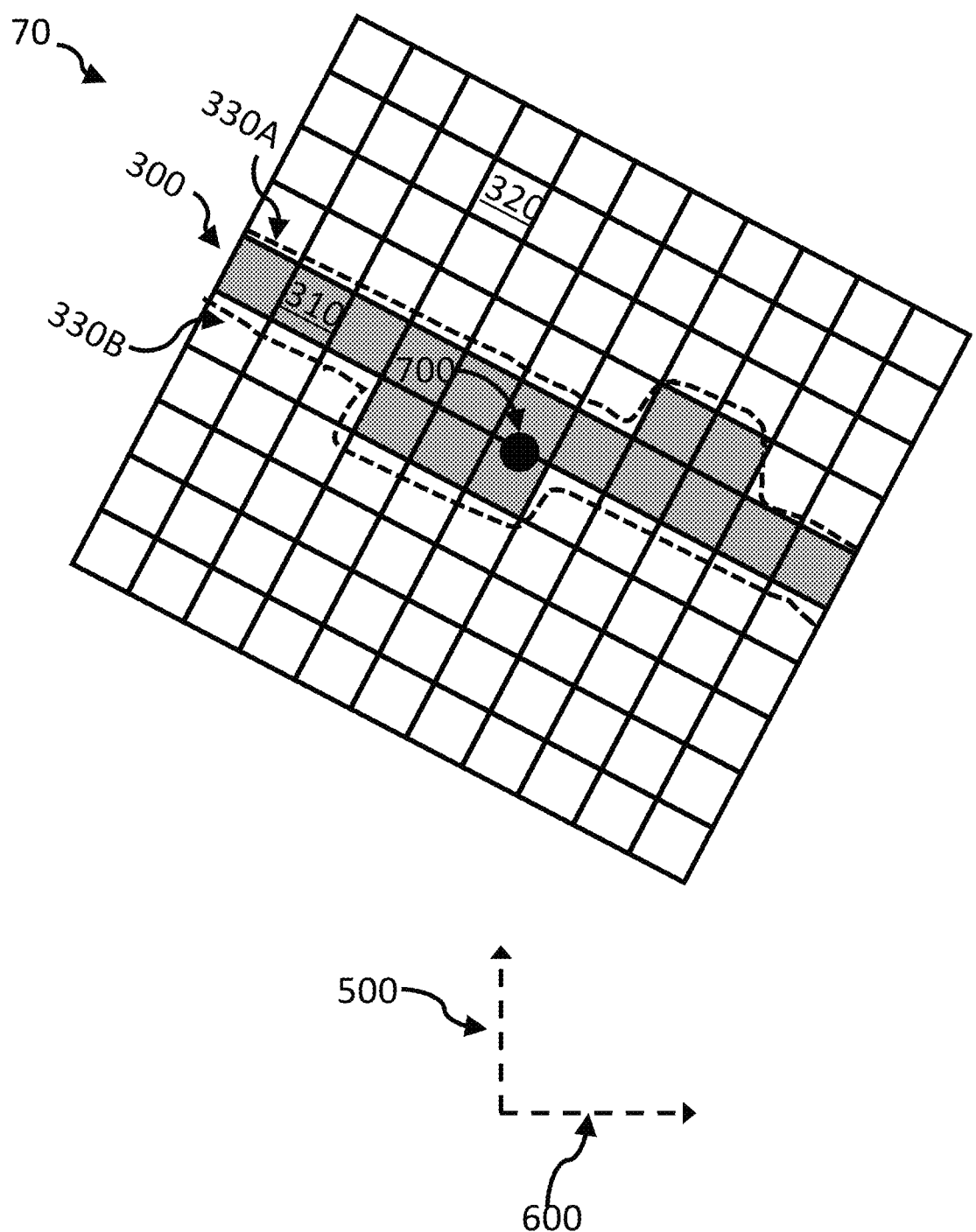
FIG. 7 illustrates a classified synthetic cross-sectional image that was generated by rotating the manually-classified image of FIG. 3 about a third axis.

Rotated images can be generated by rotating the three-dimensional manually-segmented MR images about one, two, or three axes. FIG. 7 illustrates a classified synthetic cross-sectional image 70 that was generated by rotating image 30 about a third axis 700 which extends into and out of the page of FIG. 7. The third axis 700 is orthogonal to the first and second axes 500, 600, respectively.

Combinations of any of the foregoing are possible. For example, synthetic MR images can be generated by asymmetrically stretching (e.g., in 1, 2, or 3 axes) and rotating the three-dimensional manually-segmented MR images about at least one axis. The synesthetic images can be generated by rotating the three-dimensional manually-segmented MR images about 2 or 3 axes in addition or instead of the asymmetrically stretching.

Optional step 410 can be performed to increase the number of segmented MR images to train the neural network or other artificial intelligence system in step 430. For example, there may be an insufficient number of manually-segmented images to train the neural network. The synthetic MR images can also increase the accuracy of the trained neural network by providing a wider range of classified images during training.

In step 420, the manually-segmented MR images and the optional synthetic MR images are stored on a non-transitory storage medium that is operatively coupled to the computer (e.g., computer 124) on which the neural network is to be trained in step 430. Alternatively, the storage medium can be operatively coupled to the computer on which the neural network is to be trained after the manually-segmented MR images and the optional synthetic MR images are stored on the storage medium.

Figure 8:
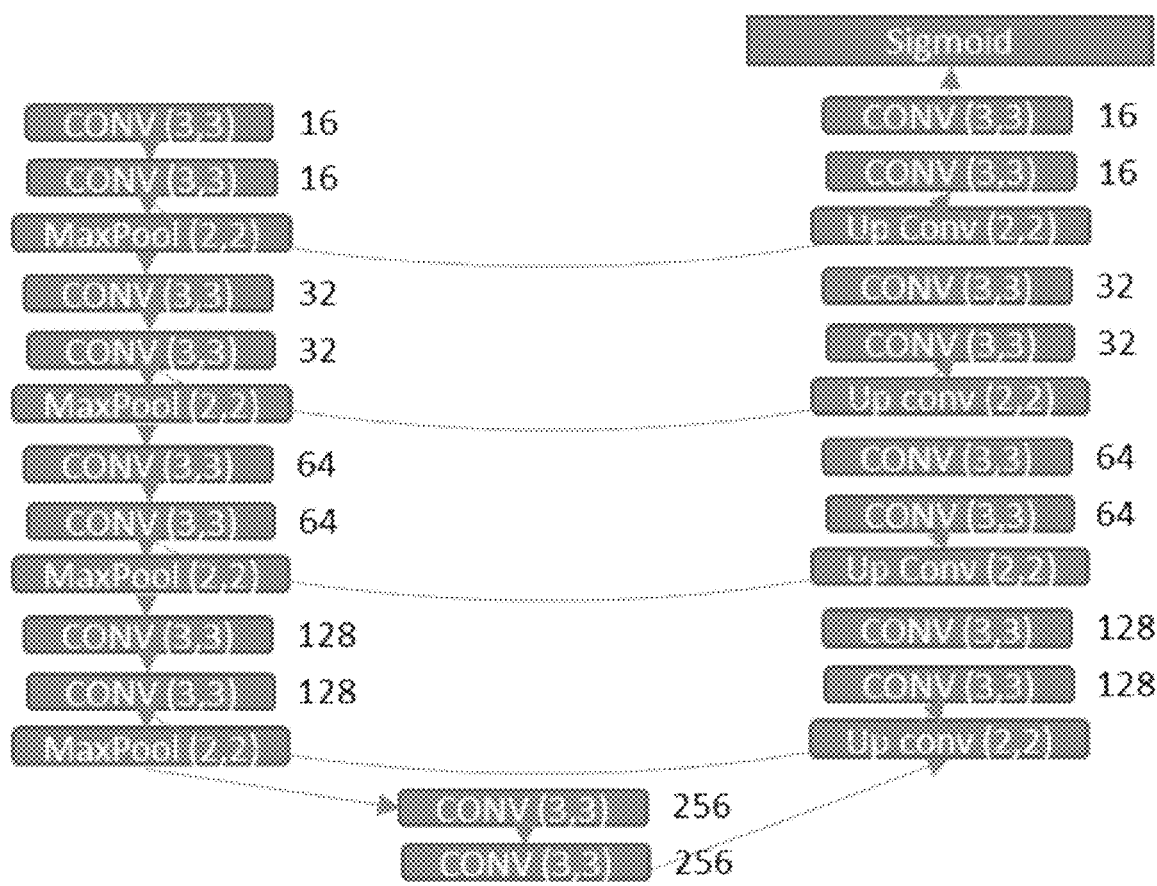
FIG. 8 illustrates an example of the architecture of a U-Net convolutional neural network.

In step 430, the neural network or other artificial intelligence system is trained using the manually-segmented MR images and the optional synthetic MR images that are stored on the storage medium in step 420. The neural network can comprise a convolutional neural network (CNN) such as a U-Net CNN. An example illustration of the architecture 80 of a U-Net CNN is illustrated in FIG. 8.

Figure 9:
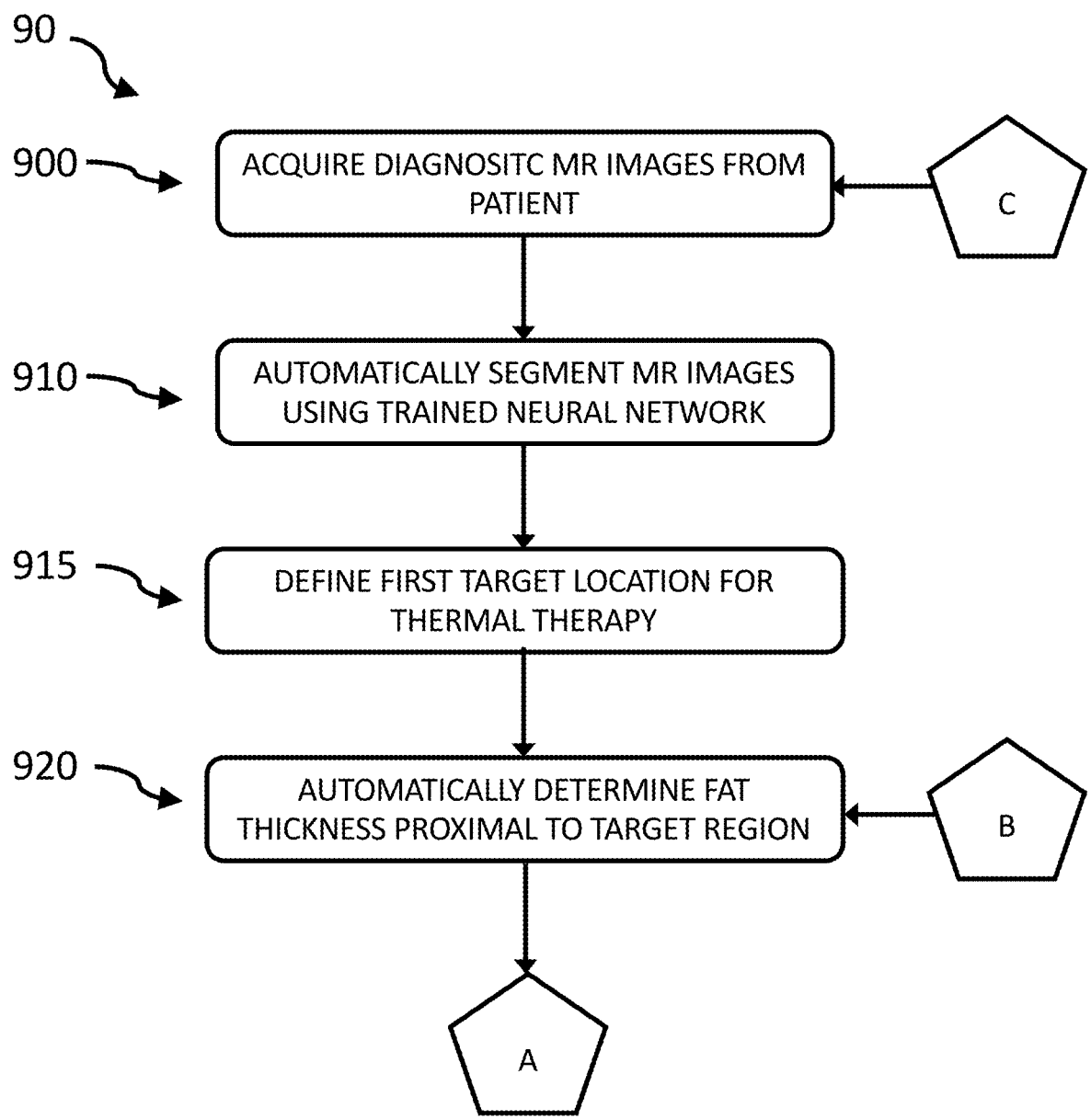
FIG. 9 is a flow chart of a method for treating a patient with a HIFU system based on the thickness of the patient's subcutaneous fat layer in the nearfield.
Figure 9:
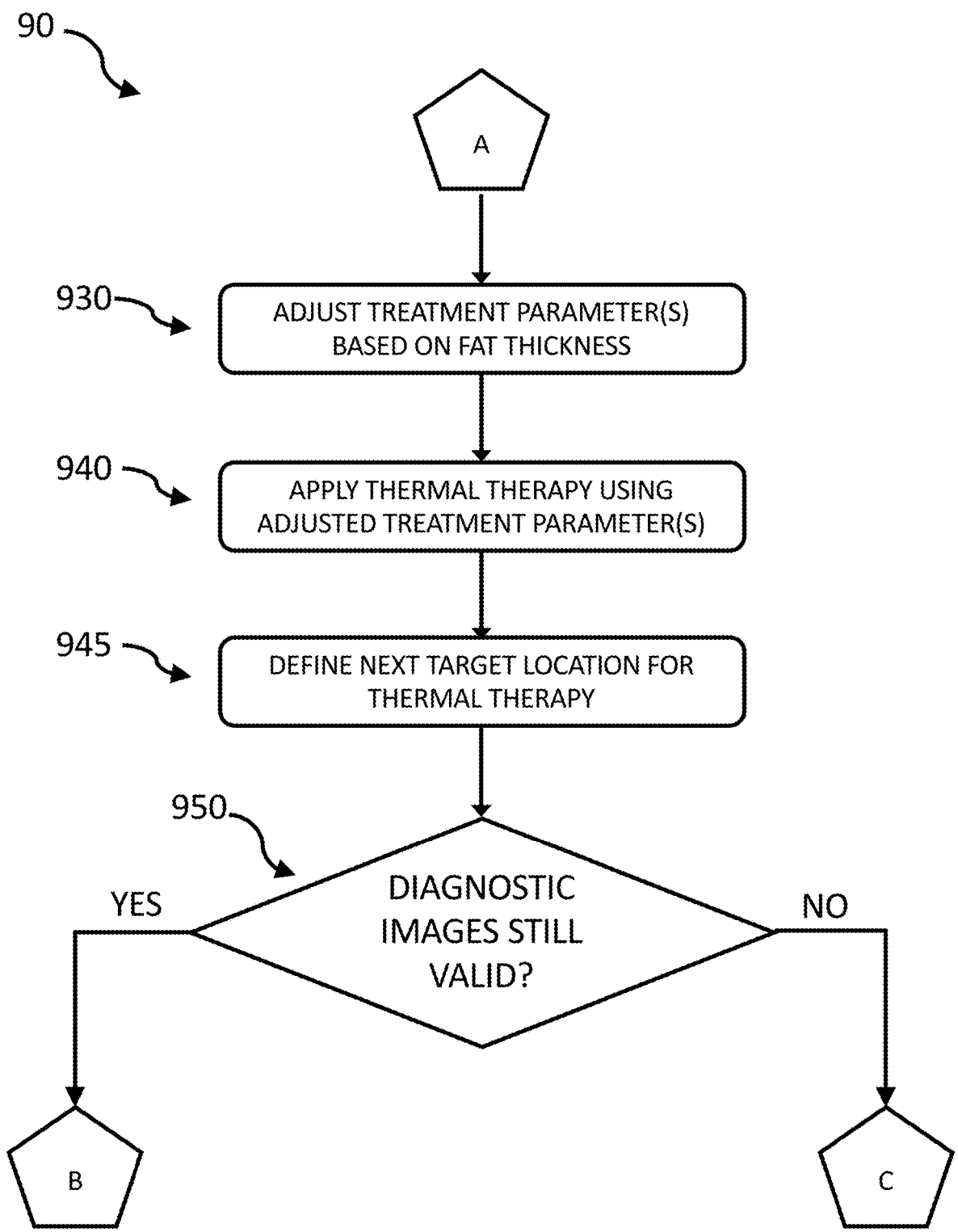

FIG. 9 is a flow chart 90 of a method for treating a patient with a HIFU system based on the thickness of the patient's subcutaneous fat layer proximal to the target treatment region according to an embodiment. In step 900, diagnostic MR images are acquired from a patient using an MR system. For example, the diagnostic MR images can be acquired using medical system 100 or MR system 102. The diagnostic MR images are preferably acquired just prior to therapeutic treatment so that the patient remains in the same position during therapeutic treatment. Alternatively, the diagnostic MR images can be acquired at a first time or date and then the therapeutic treatment can occur at a later time or date. The MR system can acquire the diagnostic MR images upon receipt of an input signal which may be generated by a computer (e.g., computer 124) that is operatively coupled thereto.

In step 910, the diagnostic MR images are automatically segmented as fat (e.g., subcutaneous fat) or non-fat using the trained neural network or other trained artificial intelligence system or machine learning (e.g., trained according to flow chart 40). The output of the automatic segmentation is a map of the subcutaneous fat layer thickness (e.g., subcutaneous fat layer thickness versus position/location).

In step 915, the target location for the first, or any subsequent, sonication is selected. The target location may be selected by the operator of the HIFU system or it may be selected automatically by an automated therapy planning algorithm. It is understood that multiple locations may be targeted in the course of the thermal therapy if the target region is large or if there are several non-contiguous target regions.

In step 920, the thickness of the patient's subcutaneous fat layer, proximal to the target location (e.g., between the energy delivery applicator and the target location), is automatically determined using the subcutaneous fat layer thickness map generated in step 910. For example, the thickness of the patient's subcutaneous fat layer corresponds to the dimensions of the voxels that are segmented or categorized as fat (e.g., as described above with respect to FIG. 3).

In step 930 (via placeholder A), one or more treatment parameters is/are adjusted based on the thickness of the patient's subcutaneous fat layer. Examples of treatment parameters that can be adjusted include the intensity of the ultrasound energy, the frequency of the ultrasound energy (e.g., the ultrasound frequency), the phase of the ultrasound energy, the sonication duration, and/or the minimum period between consecutive sonications. One or more of these treatment parameters can be adjusted by the safety control algorithm.

For example, the safety control algorithm simulates the temperature rise in and/or thermal dose to the patient's tissue within the path of the thermal energy beam (e.g., ultrasound beam), sometimes referred to as the nearfield, using the bioheat transfer equation. Current systems estimate the tissue as homogenous media having an average tissue property or as rectangular tissue slabs of a pre-defined thickness. In one embodiment, the actual thickness of the patient's subcutaneous fat layer, which may vary spatially, can be used as an input to the bioheat transfer equation. An example of the bioheat transfer equation is:

$$\rho c_t \frac{\partial T}{\partial t} = \nabla \cdot (k_t \nabla T) - w_b c_b (T - T_b) + Q \qquad (1)$$

where $\rho$ is tissue density; $c_t$ is tissue specific heat; $k_t$ is thermal conductivity; $w_b$ is blood perfusion; $c_b$ is the blood specific heat; $T_b$ is the blood temperature; T is the tissue temperature; and Q is the ultrasound heat deposition. Tissue-specific parameters (e.g. $c_t$, $k_t$, and $w_b$) take different values in regions made of fat, muscle or other tissues. The subcutaneous fat thickness defines the region where the parameters take value specific to fat. For example, when the patient's subcutaneous fat layer is relatively thick (e.g., compared to a predetermined thickness such as an average subcutaneous fat thickness which may vary based on gender), more ultrasound energy is absorbed which can cause the temperature in the nearfield region to increase faster than a corresponding temperature increase for a subcutaneous fat layer having a thinner fat layer (e.g., the predetermined thickness). Since the nearfield region temperature increases faster, longer cooldown periods between sonications may be needed during thermal therapy application, as determined by the safety control algorithm, to ensure that the maximum temperature in the nearfield region stays below a predetermined maximum temperature. The predetermined maximum temperature can correspond to a temperature at which damage to body tissue or cells occurs. In another example, when the patient's subcutaneous fat layer is relatively thin (e.g., compared to the predetermined thickness such as an average subcutaneous fat thickness which may vary based on gender), less ultrasound energy is absorbed which can cause the temperature in the nearfield region to increase slower than a corresponding temperature increase for a subcutaneous fat layer having a thicker fat layer (e.g., the predetermined thickness). Since the nearfield region temperature increases slower, shorter cooldown periods between sonications may be used, as determined by the safety control algorithm, while still ensuring that the maximum temperature in the nearfield region stays below the predetermined maximum temperature, thus completing the thermal therapy in a shorter time.

In another example, the intensity or power of the ultrasound energy can be automatically adjusted based on the actual thickness of the patient's subcutaneous fat layer. For example, since a thicker subcutaneous fat layer absorbs more energy (e.g., the subcutaneous fat layer is thicker compared to a predetermined thickness such as an average subcutaneous fat thickness which may vary based on gender), the ultrasound power can be increased to compensate for the absorbed energy in patients that have relatively thick subcutaneous fat layers. Likewise, the ultrasound power can be decreased to compensate for the absorbed energy in patients that have relatively thin subcutaneous fat layers (e.g., the subcutaneous fat layer is thin compared to the predetermined thickness). In some embodiments, the system can automatically propose or suggest the ultrasound power based on the patient's subcutaneous fat layer thickness.

In another example, the frequency of the ultrasound energy can be automatically adjusted based on the actual thickness of the patient's subcutaneous fat layer. In general, lower-frequency energy is absorbed less in fat than higher-frequency energy. Therefore, the frequency of the ultrasound energy can be automatically decreased when the patient has a relatively thick subcutaneous fat layer (e.g., the subcutaneous fat layer is thicker compared to a predetermined thickness such as an average subcutaneous fat thickness which may vary based on gender). Likewise, the frequency of the ultrasound energy can be automatically increased when the patient has a relatively thin subcutaneous fat layer (e.g., the subcutaneous fat layer is thin compared to the predetermined thickness).

Figure 10:
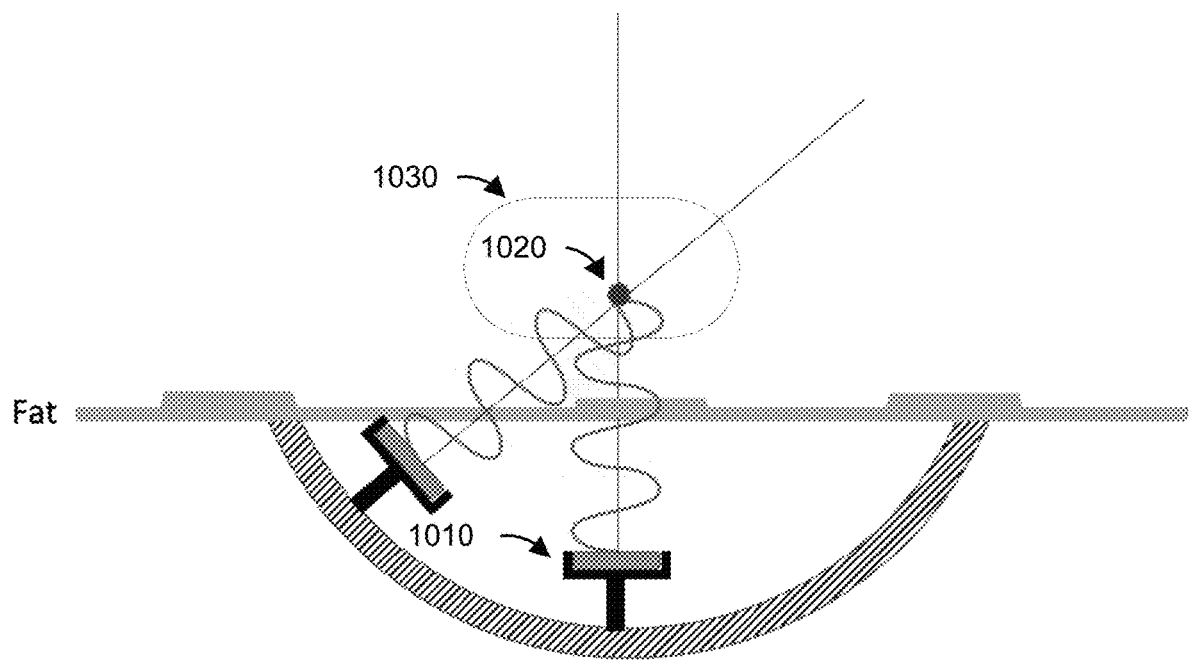
FIG. 10 illustrates how the relative phase of ultrasound energy generated by ultrasound transducer elements can be adjusted based on the thickness of the subcutaneous fat layer in the nearfield.

In another example, the relative phase of the ultrasound energy can be automatically adjusted based on the actual thickness of the patient's subcutaneous fat layer. Since the energy travels through different media at different speeds, the relative phase of the ultrasound energy can be adjusted to account for the thickness of the patient's subcutaneous fat layer so that the ultrasound energy has the desired phase at the treatment region, which can improve the focus of the ultrasound energy beam. For example, the relative phase of the ultrasound energy generated by each ultrasound transducer element 1010 in the ultrasound transducer element array is controlled so that the ultrasound energy, after passing through a non-spatially uniform subcutaneous fat layer having a known thickness, is in phase (or has a desired phase offset to spread the focus of the beam) at the target location 1020 in the treatment region 1030, as illustrated in FIG. 10.

In step 940, ultrasound thermal therapy is applied to the target treatment region. The ultrasound thermal therapy can be applied according to a treatment plan, as discussed above. In an embodiment, the cooling time between sonications or during a given sonication can be adjusted due to the updated safety algorithm (e.g., updated in step 930), which can be updated based on the actual thickness of the patient's subcutaneous fat layer. Additionally or alternatively, the ultrasound thermal therapy parameters (e.g., power, frequency, and/or phase) can be adjusted using the updated treatment parameters (e.g., updated in step 930). The HIFU system can generate ultrasound energy for thermal therapy upon receipt of an input signal which may be generated by a computer (e.g., computer 124) that is operatively coupled thereto.

In step 945, the next target location is determined. This step may be performed by the operator of the HIFU system or it may be selected automatically by an automated therapy planning algorithm. Then, in step 950, it is determined whether the MR image previously segmented in step 910 is still valid. If the MR image is still valid, the flow chart returns to step 920 (via placeholder B) to automatically determine the subcutaneous fat thickness proximal to the new target location and the flow chart 90 continues from that point on. If the MR image is no longer valid, a new MR image of the patient is acquired in step 900 (via placeholder C) and flow chart 90 continues from that step. One reason why the MR image is no longer valid could be that the patient has moved since the previous MR image was acquired. Another reason could be that the new target location is not within the field of view of the original MR image. Other reasons are known to those of skill in the art.

The steps in flow chart 90 can be repeated during thermal therapy treatment. For example, the steps in flow chart 90 can be repeated if multiple sonications at different target treatment locations are required in the thermal therapy. The patient's subcutaneous fat layer thickness can be automatically determined with respect to each target treatment volume within the target treatment region. MR imaging of the target treatment volume generates a cross-sectional image of the target treatment volume including the patient's subcutaneous fat layer. As the target treatment location changes, the corresponding cross-sectional image of the target treatment volume changes. The thickness of the patient's subcutaneous fat layer can vary between cross-sectional images and/or within a given cross-sectional image. Thus, the treatment parameters can be adjusted (e.g., in step 930) multiple times during and/or throughout treatment. Adjusting the treatment parameters based on the actual thickness of the patient's subcutaneous fat layer can increase safety (e.g., by updating an input to the safety control algorithm to prevent overheating of the nearfield region)

Though embodiments of the invention have been described with respect to segmenting fat (e.g., subcutaneous fat) from non-fat tissue, it is noted that the principles of this disclosure are also applicable to segmenting other types of tissue and/or bone. For example, the principles of this disclosure are applicable to segmenting tendons, skin, muscle, fibroids, organs, joints, bones, and/or other portions of human anatomy.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A method for controlling delivery of thermal therapy, comprising:
    acquiring magnetic resonance (MR) images, with an MR imaging system, of tissue proximal to a target treatment region in a patient, the tissue including a non-spatially uniform subcutaneous fat layer;
    in a computer comprising a hardware-based processor, automatically determining an actual thickness of the subcutaneous fat layer using a trained neural network, the neural network trained using manually-segmented MR images from previous patients;
    in the computer, automatically adjusting a set of treatment parameters based on the actual thickness of the subcutaneous fat layer; and
    delivering thermal therapy to the target treatment region with a high-intensity focused ultrasound (HIFU) system based on the adjusted set of treatment parameters.

2. The method of claim 1, wherein the set of treatment parameters comprises an input to a safety control algorithm.

3. The method of claim 2, wherein the safety control algorithm ensures a predetermined maximum temperature and/or a predetermined maximum thermal dose of tissue between the target treatment region and a therapeutic applicator of the HIFU system.

4. The method of claim 2, wherein the safety control algorithm increases a cooldown time between thermal therapy sonications when the actual thickness of the subcutaneous fat layer is higher than a predetermined thickness, the predetermined thickness corresponding to an average subcutaneous fat layer thickness for the gender of the patient.

5. The method of claim 2, wherein the safety control algorithm decreases a cooldown time between thermal therapy sonications when the actual thickness of the subcutaneous fat layer is lower than the predetermined thickness.

6. The method of claim 1, wherein the set of treatment parameters comprises a frequency of ultrasound energy generated by the HIFU system.

7. The method of claim 1, wherein the set of treatment parameters comprises a power of ultrasound energy generated by the HIFU system.

8. The method of claim 7, wherein the power of the ultrasound energy increases when the actual thickness of the subcutaneous fat layer is higher than a predetermined thickness, the predetermined thickness corresponding to an average subcutaneous fat layer thickness for the gender of the patient.

9. The method of claim 8, wherein the power of the ultrasound energy decreases when the actual thickness of the subcutaneous fat layer is lower than the predetermined thickness.

10. The method of claim 1, wherein the set of treatment parameters comprises a relative phase of ultrasound energy generated by each ultrasound transducer element in an array of ultrasound transducer elements.

11. A system for delivering ultrasound thermal therapy comprising:
- a magnetic resonance (MR) imaging system;
- a high-intensity focused ultrasound (HIFU) system comprising an array of ultrasound transducer elements;
- a computer comprising a hardware-based processor, the computer operatively coupled to the MR imaging system and to the HIFU system; and
- a non-transitory storage medium comprising computer-readable instructions that, when executed by the processor, cause the processor to:
  - send a first output signal to the MR system to acquire MR images of tissue proximal to a target treatment region in a patient, the tissue including a non-spatially uniform subcutaneous fat layer,
  - automatically determine an actual thickness of the subcutaneous fat layer using a trained neural network, the neural network trained using manually-segmented MR images from previous patients,
  - adjust a set of treatment parameters based on the actual thickness of the subcutaneous fat layer, and
  - send a second output signal to the HIFU system to deliver thermal therapy to the target treatment region based on the adjusted set of treatment parameters.

12. The system of claim 11, wherein the set of treatment parameters comprises an input to a safety control algorithm.

13. The system of claim 12, wherein the safety control algorithm ensures a predetermined maximum temperature and/or a predetermined maximum thermal dose of tissue between the target treatment region and a therapeutic applicator of the HIFU system.

14. The system of claim 12, wherein the safety control algorithm increases a cooldown time between thermal therapy sonications when the actual thickness of the subcutaneous fat layer is higher than a predetermined thickness, the predetermined thickness corresponding to an average subcutaneous fat layer thickness for the gender of the patient.

15. The system of claim 14, wherein the safety control algorithm decreases a cooldown time between thermal therapy sonications when the actual thickness of the subcutaneous fat layer is lower than the predetermined thickness.

16. The system of claim 11, wherein the set of treatment parameters comprises a frequency of ultrasound energy generated by the HIFU system.

17. The system of claim 11, wherein the set of treatment parameters comprises a power of ultrasound energy generated by the HIFU system.

18. The system of claim 17, wherein the power of the ultrasound energy increases when the thickness of the subcutaneous fat layer is higher than a predetermined thickness, the predetermined thickness corresponding to an average subcutaneous fat layer thickness for the gender of the patient.

19. The system of claim 18, wherein the power of the ultrasound energy decreases when the thickness of the subcutaneous fat layer is lower than the predetermined thickness.

20. The system of claim 11, wherein the set of treatment parameters comprises a relative phase of ultrasound energy generated by each ultrasound transducer element in the array of ultrasound transducer elements.

* * * * *